United States Patent
Yoo et al.

(10) Patent No.: US 9,585,688 B2
(45) Date of Patent: Mar. 7, 2017

(54) TISSUE EXPANDER

(75) Inventors: James J. Yoo, Winston-Salem, NC (US); Anthony Atala, Winston-Salem, NC (US); Paul Scarpinato, Clemmons, NC (US); Sang Jin Lee, Winston-Salem, NC (US); Mitchell Ladd, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 974 days.

(21) Appl. No.: 12/986,771

(22) Filed: Jan. 7, 2011

(65) Prior Publication Data

US 2011/0172683 A1    Jul. 14, 2011

Related U.S. Application Data

(60) Provisional application No. 61/293,406, filed on Jan. 8, 2010.

(51) Int. Cl.
   *A61B 17/322* (2006.01)
   *A61B 17/00* (2006.01)

(52) U.S. Cl.
   CPC ............ *A61B 17/322* (2013.01); *A61B 90/02* (2016.02); *A61B 2017/00969* (2013.01); *A61B 2017/3225* (2013.01)

(58) Field of Classification Search
   CPC ................. A61B 5/065; A61B 17/322; A61B 2017/3225; A61B 90/02; A61F 2250/0012; A63B 5/11
   USPC ...................... 623/15.12, 915; 600/587–595; 73/862.392
   See application file for complete search history.

(56) References Cited

U.S. PATENT DOCUMENTS

| | | | | |
|---|---|---|---|---|
| 4,192,321 A | * | 3/1980 | Korber | A61C 19/04 600/589 |
| RE30,344 E | * | 7/1980 | McNeil | A63B 5/11 482/27 |
| 5,015,584 A | * | 5/1991 | Brysk | 623/15.12 |
| 5,127,412 A | | 7/1992 | Cosmetto et al. | |
| 5,219,352 A | | 6/1993 | Atkinson | |
| 5,571,138 A | | 11/1996 | Blomqvist et al. | |
| 5,573,784 A | | 11/1996 | Badylak et al. | |
| 5,914,264 A | | 6/1999 | Korman | |
| 6,051,750 A | | 4/2000 | Bell | |
| 6,206,931 B1 | | 3/2001 | Cook et al. | |

(Continued)

FOREIGN PATENT DOCUMENTS

WO    WO 2006/113382 A2    4/2006

OTHER PUBLICATIONS

International Search Report and Written Opinion, PCT/US11/20540, mailed Mar. 22, 2011.

(Continued)

*Primary Examiner* — Brian Pellegrino
(74) *Attorney, Agent, or Firm* — Myers Bigel, P.A.

(57) ABSTRACT

Provided herein is a tissue stretching device including a tissue clamping member defining an area in a Z plane, wherein the tissue clamping member is configured to hold tissue parallel to the Z plane. Methods of use of the tissue stretching device to stretch a tissue as well as for culturing organized tissues are also provided. Stretched and/or cultured tissues produced by these processes are also provided, as well as methods of treatment making use of the same.

22 Claims, 5 Drawing Sheets

(56) References Cited

U.S. PATENT DOCUMENTS

| | | |
|---|---|---|
| 6,364,908 B1 | 4/2002 | Ysebaert |
| 6,485,723 B1 | 11/2002 | Badylak et al. |
| 6,568,235 B1 * | 5/2003 | Kokish .......................... 606/1 |
| 6,998,418 B1 | 2/2006 | Sung et al. |
| 8,052,622 B2 * | 11/2011 | Egorov et al. ............... 600/591 |
| 2002/0128711 A1 | 9/2002 | Tanagho et al. |
| 2003/0009178 A1 | 1/2003 | Fields et al. |
| 2003/0199083 A1 * | 10/2003 | Vilendrer ............... C12M 21/08 435/297.2 |
| 2008/0221682 A1 | 9/2008 | Aray |

OTHER PUBLICATIONS

Ladd MR et al. Bioreactor maintained living skin matrix. Tissue Engineering: Part A. 2009; 15(4): 861-868.

* cited by examiner

TISSUE EXPANDER

RELATED APPLICATIONS

This application claims the benefit under 35 U.S.C. §119(e) of U.S. Provisional Patent Application Ser. No. 61/293,406, filed Jan. 8, 2010, the disclosure of which is incorporated herein by reference in its entirety.

STATEMENT OF GOVERNMENT SUPPORT

This work was supported by grant no. W81XWH-08-1-0764 from the Department of Defense. The U.S. Government has certain rights in this invention.

FIELD OF THE INVENTION

The present invention is in the field of tissue engineering.

BACKGROUND OF THE INVENTION

Skin grafting is an essential component of reconstructive surgery after burns, trauma, tumor excision, and correction of congenital anomalies. There are approximately 1 million burns per year in the U.S. alone, which result in about 100,000 admissions to burn units, about ⅓ of which require skin grafting. Skin grafting in reconstructive surgery is often required to alleviate deformity. The best possible skin available for grafting would be skin from the same patient taken from a donor site elsewhere on the body (referred to as an autograft). Suitable skin graft donor sites, however, are limited not only by body surface area, but can also be affected by previous graft harvest or trauma. Because of the importance of the skin in preventing infection, either the donor skin must be used to cover a larger area than it originally covered or some suitable replacement material must be used.

Devices useful for stretching tissue such as skin are therefore needed to increase the area available for grafting.

SUMMARY OF THE INVENTION

Provided herein is a tissue stretching device, including: a tissue clamping member defining an area in a Z plane, wherein the tissue clamping member is configured to hold tissue parallel to the Z plane, wherein the tissue clamping member is configured to expand in area along the Z plane; a displacement sensor operatively associated with the tissue clamping member, the displacement sensor configured to detect the amount of expansion of the tissue by the tissue clamping member; and a controller operatively associated with the tissue clamping member, wherein the controller operates an actuator connected to the tissue clamping member to thereby stretch the tissue along the Z plane. In some embodiments, the tissue is skin tissue or muscle tissue.

In some embodiments, the controller is operatively associated with a force sensor, whereby the force sensor senses the force applied to the tissue in the tissue clamping member upon the application of force by the actuator connected thereto.

In some embodiments, the tissue clamping member is enclosed in a chamber configured to hold media, wherein the media is in fluid contact with at least a portion of the tissue.

In some embodiments, the tissue clamping member has four sides along the Z plane. In some embodiments, two adjoining sides of the tissue clamping member are fixed relative to the chamber, and the other two adjoining sides are movable along the Z plane.

In some embodiments, the device further includes a media reservoir, and in some embodiments the chamber includes a media inlet and media outlet in fluid communication with the media reservoir.

In some embodiments, the chamber further includes a gas inlet configured to provide a gas to the tissue.

Also provided are methods of stretching a tissue including: clamping the tissue into the tissue clamping member of the device as provided herein; and stretching the tissue with the device to thereby stretch the tissue (e.g., skin tissue or muscle tissue).

Further provided are methods of treating a skin wound of a subject in need thereof, including: providing skin tissue; stretching the skin tissue with the device of claim 1 to form stretched skin tissue; and then grafting the stretched skin tissue onto the subject, to thereby treat the skin wound. In some embodiments, the skin tissue is autologous or allogeneic.

Still further provided are methods of culturing organized tissue, including: (a) providing cells on a support, wherein the support is clamped into the tissue clamping member of the device as provided herein; then (b) cyclically stretching and relaxing the support at least twice along a first (X) axis during a first time period; (c) cyclically stretching and relaxing the support at least twice along a second (Z) axis during the first time period; and then (d) maintaining the support in a substantially static position during a second time period; and then (e) repeating steps (b) and (d) for a number of times sufficient enhance the functionality of the tissue or to produce organized tissue on the solid support from the cells.

Cultured tissue (e.g., skin tissue or muscle tissue) produced by the processes described herein are also provided.

The foregoing and other objects and aspects of the present invention are explained in greater detail in the drawings herein and the specification set forth below.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF THE PREFERRED EMBODIMENTS

Figure 1:
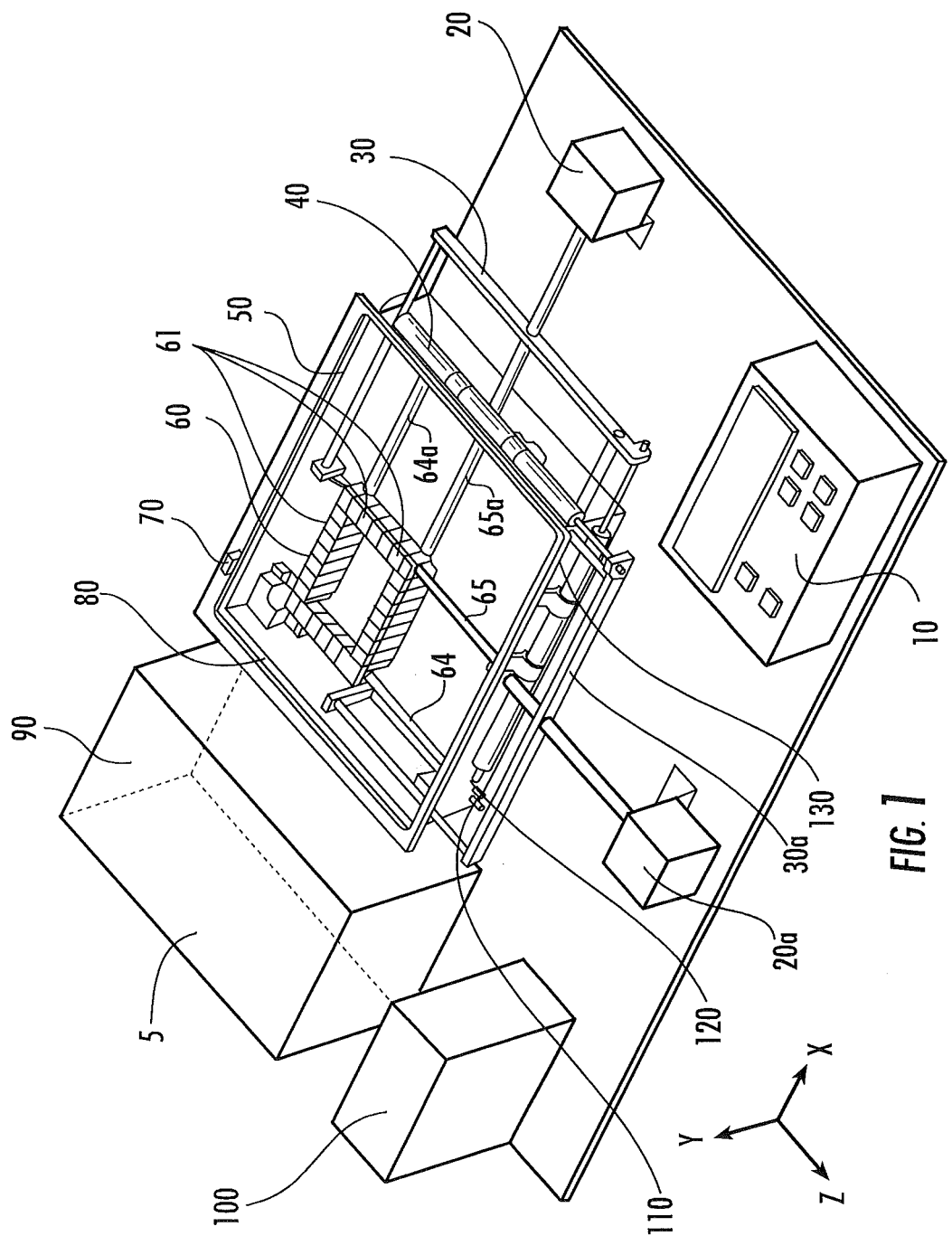
FIG. 1 provides a top perspective view of an embodiment of the tissue expander.

Provided herein and further described below are devices and methods useful for the culturing, conditioning and/or stretching of tissues. Tissues which may be conditioned/stretched/cultured include intact tissues harvested from a suitable donor, cells harvested from a suitable donor and seeded onto a suitable support, which include stem cells or precursor cells which may be undifferentiated or differentiated prior to seeding onto a suitable support, etc.

Like numbers refer to like elements throughout. In the figures, the thickness of certain lines, layers, components, elements or features may be exaggerated for clarity.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Tissue produced as described herein may be used for treatment such as the replacement and/or reconstruction of damaged tissue in a patient. Such tissue may be grafted or implanted into the subject using procedures known in the art.

"Treat" refers to any type of treatment that imparts a benefit to a subject, e.g., a patient afflicted with a trauma or disease. Treating includes actions taken and actions refrained from being taken for the purpose of improving the condition of the patient (e.g., the promotion of healing and/or formation of tissues on a patient in need thereof, the relief of one or more symptoms, etc.). In some embodiments, treating includes reconstructing skin tissue (e.g., where such tissue has been damaged or lost by injury or disease) by grafting or implanting tissues onto a subject in need thereof.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

The tissue to be stretched is preferably human for use in human recipients, but veterinary use is also encompassed by the invention, as noted above. Tissue scaffolds (e.g., decellularized tissues) may also be used, and may be seeded with cells, if desired. Tissues and/or cells seeded onto tissue scaffolds may be autologous (i.e., from the very subject to which they will be applied) syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the subject to be treated) and isogeneic (i.e., a genetically identical but different subject, e.g., from an identical twin). Tissues and/or cells may be obtained from, e.g., a donor (either living or cadaveric) or derived from an established cell strain or cell line. For example, cells may be harvested from a donor using standard biopsy techniques known in the art. For allogeneic transplant into a patient, tissue as described herein may be matched or tissue-typed in accordance with known techniques, and/or the subject may be administered immune suppressive agents to combat tissue transplant rejection, also in accordance with known techniques.

In some embodiments, a segment of vertebrate tissue is obtained (e.g., skin tissue), positioned in an artificial cell growth medium containing sufficient nutrients to maintain growth of cells of the tissue segment. The tissue segment is then subjected to stretching forces while the tissue segment is in the medium. In various embodiments of the invention, the stretching forces are dynamic or static, orthogonal or radial, or constant or varying. Tissue may be placed on an elastic membrane, if desired. See U.S. Pat. No. 6,364,908 to Ysebaert.

Tissue produced as described herein may also be used in vitro, in the apparatus described herein or in a separate apparatus, to examine the pharmacological or toxicological properties of compounds of interest, for example, by adding the compound of interest to a culture medium in which the tissue is immersed, and examining the histological or mechanical properties of the tissue as compared to a control tissue without the presence of the compound.

In the following description of various embodiments of the invention, the invention is described in most cases as being practiced with a human tissue autograft. However, the invention is not so limited and can be used for both allografts (within the same species, but with the donor and recipient being different individuals) and xenografts (donor and recipient from different species). Additionally, the invention is not limited to preparation of human tissue, since it can be advantageously practiced to produce large amounts of normal tissue of various vertebrates, either for veterinary use as autografts or allografts, or for use in the production of xenografts (which would normally require suppression of the immune system of the recipient when the product tissue is used as a graft), since even the temporary protection against infection and sepsis provided by a xenograft may save the life of the recipient organism. For veterinary or xenograft use, the donor tissue can be obtained from any vertebrate, preferably one related as closely as possible to the recipient. Non-exclusive examples include tissue from humans, other primates, cattle and other domesticated bovines, pigs, hogs, cats, dogs, sheep, goats, birds, and reptiles.

A segment of vertebrate tissue (graft donor segment) is obtained by any of the techniques normally available for this purpose, usually surgical excision or use of a dermatome (for split-thickness skin). If a dermatome (i.e., any plane-like device for removing skin from a subject) is used, the thickness of the layer should be selected to ensure that at least some of the dermal layer is present. This thickness will vary from species to species and even from location to location on the body of an individual. A typical setting for a dermatome used to prepare split-thickness human skin is about 12/1000th of an inch (about 0.3 mm). The skin segment is obtained so that both dermal and epidermal layers are present in the detached segment. The dermal layer can be either complete (full-thickness skin) or incomplete (split-thickness skin), but it is preferred that some of the dermal layer be present.

Full-thickness skin segments are typically obtained by surgical excision, while split-layer skin segments are typically obtained by a dermatome. Both of these techniques, as well as other general techniques in the field of skin grafting, as described in Chapter 1 (pp. 1-90) of Grabb and Smith, Plastic Surgery, Little Brown & Company, Boston, Mass., USA, 4th Ed. (1991), James W. Smith and Sherrel J. Aston, eds. The detached skin is normally transferred directly to a culture medium, and in most cases is not allowed to dry out before being positioned in the medium.

The shape of the detached skin segment is not material to the practice of the invention, but certain shapes will be better suited to individual specific apparatus variations described here (e.g., square, rectangular, substantially square or substantially rectangular). See also U.S. Pat. No. 5,914,264 to Korman.

The size of the donor tissue segment is generally selected for the convenience of use with the apparatus in which it will be stretched and may also vary depending on the availability of donor skin tissue of the same type as that being replaced. Typical human skin segments are from 1×1 cm to 10×30 cm, but can vary significantly depending on the availability of donor skin. There is generally no impact of graft size on the method of the invention, so that surgical and other procedures generally are more important in determining tissue size. For ease of handling in surgical skin grafting, segments ranging in size from 5×5 cm to 15×15 cm may be used; however, other suitable sizes may be used.

Preparation and use of artificial cell-growth media containing sufficient nutrients to maintain growth of cells of a skin segment are well-established techniques and need not be described here in detail. Such media are also referred to as nutrient media or tissue-culture media. Whether any given medium will be satisfactory (if not already known) can easily be determined experimentally using the procedures for skin growth set out in the examples below. Many such media are commercially available, such as Dulbecco's modified Eagle's medium (DMEM) with 10% added fetal calf serum. Other suitable media include basal medium (Eagle) with Hanks's BSS (85%) supplemented with calf serum (15%) and Ham's F12 medium (90%) supplemented with fetal bovine serum (10%). When serum is used to supplement an artificial medium, fetal serum is preferred, especially fetal serum from the same species as the recipient of the graft. When this is not possible or ethically desirable, the recipient's own serum can be used. For a number of media that can be used to grow skin tissue, see, for example, the media formulations section of any volume of the American Type Culture Collection publication entitled Catalogue of Cell Lines & Hybridomas (e.g., 5th edition, 1985, pages 265-273). This ATCC publication also contains information (in connection with specific skin-derived cell lines) on which media are best for use with tissue or cell cultures derived from skin.

According to some embodiments, the tissue segment is subjected to stretching forces while in the medium. Here "stretching forces" means a force or forces applied to the segment in one or more directions parallel to the plane of the skin surface. In preferred embodiments, the tissue is stretched in two directions along the plane of the tissue (the "Z plane" as used herein, comprised of the Z and X axis, as shown in FIG. 1), which two directions are or are substantially perpendicular or orthogonal.

As illustrated in FIG. 1, in some embodiments a device 5 includes a controller (10), a pair of motors or drives (20, 20a), a pair of drive rod assemblies (30, 30a), a pair of displacement sensors (40, 40a), a chamber (50), a tissue clamping member (60) comprised of individual clamps and support pairs as discussed below, a force sensor (70), a media outlet (80), a media reservoir (90), a device for metering air/$CO_2$ mixture (100), a media inlet (110), an air/$CO_2$ mixture inlet (120), and a chamber top (130). For clarity of illustration, wires or leads interconnecting sensors, motors, controllers, power supplies and the like are not shown.

In some embodiments, a tissue clamping member (60) defines an area in a Z plane, wherein the tissue clamping member (60) is configured to hold tissue parallel to the Z plane, wherein the tissue clamping member (60) is configured to expand in area along the Z plane; a displacement sensor (40) operatively associated with the tissue clamping member (60), the displacement sensor (40) configured to detect the amount of expansion of the tissue by the tissue clamping member (60); and a controller (10) operatively associated with the tissue clamping member (60), wherein the controller (10) operates an actuator (20) connected to the tissue clamping member (60), to thereby stretch the tissue along the Z plane.

In some embodiments, the tissue is skin tissue or muscle tissue. In some embodiments, the controller (10) is operatively associated with a force sensor (70), whereby the force sensor (70) senses the force applied to the tissue in the tissue clamping member (60) upon the application of force by the actuator (30) connected thereto.

In some embodiments, the tissue clamping member (60) is enclosed in a chamber (50) configured to hold media, wherein the media is in fluid contact with at least a portion of the tissue.

In some embodiments, the tissue clamping member (60) has four sides along the Z plane. In some embodiments, two adjoining sides of the tissue clamping member are fixed relative to the chamber (50), and the other two adjoining sides are movable along the Z plane.

The controller (10) may be programmed to adjust the force applied by a motor (20 or 20a) and corresponding drive assembly (30 or 30a), or other actuator, operatively associated with the clamping member (60) based upon present times and/or force sensed by the force sensor (70). A displacement sensor (40, 40a) may also be provided, which is configured to measure the linear displacement of the tissue held in the clamping member (60), and may also be operatively associated with the controller (10).

In some embodiments, the clamping member (60) is provided in a chamber (50) configured to hold media, wherein said media is in fluid contact with the clamping member (60). A top (130) may also be provided, which top is configured to seal the chamber (50).

The chamber (50) may include a media inlet (110) and media outlet (80) to allow media change/replenishment without the need to open the chamber (50). The media inlet (110) may in some embodiments be in fluid connection with a media reservoir (90) which is configured to hold fresh, sterile media.

A gas inlet (120) may also be provided on the chamber (50). Any suitable gas such as air or an air/5% $CO_2$ mixture may be used in order to promote tissue growth. The gas inlet may be operatively connected to a device for metering the gas (100), as well as a HEPA filter to remove contaminates (not shown). A gas outlet may also be provided on the chamber (not shown).

Figure 2:
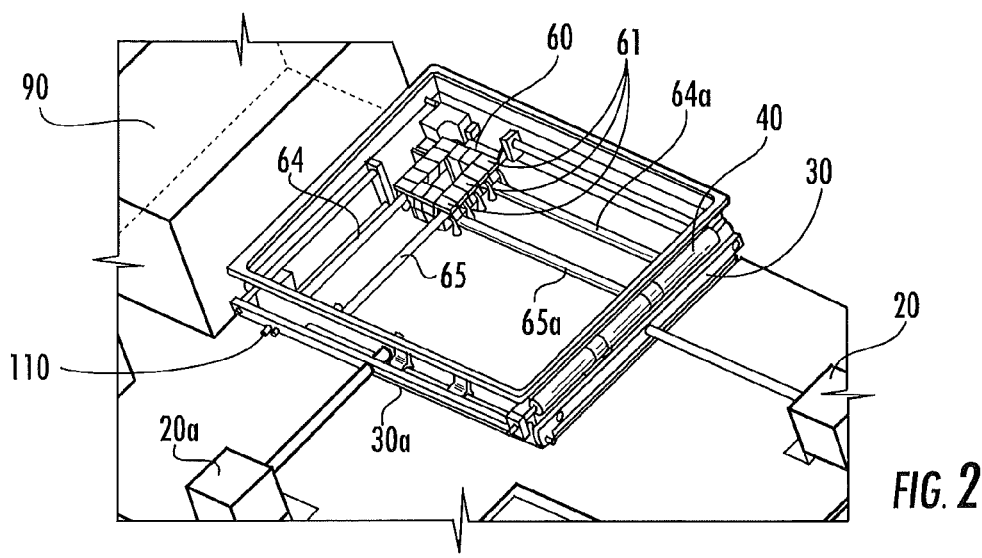
FIGS. 2-7 are cutout views of the tissue expander embodiment presented in FIG. 1 showing movement of the tissue clamping member (60) along the Z axis.
Figure 3:
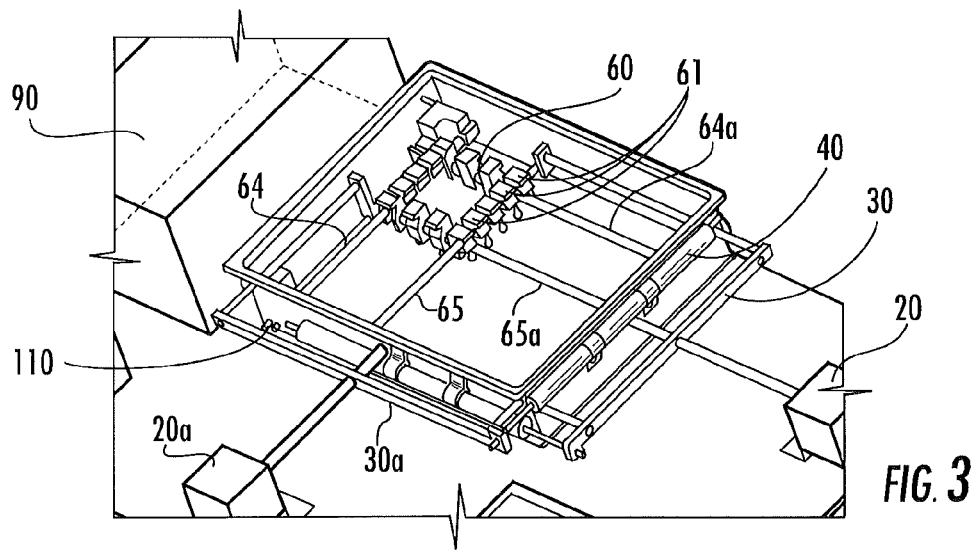
Figure 4:
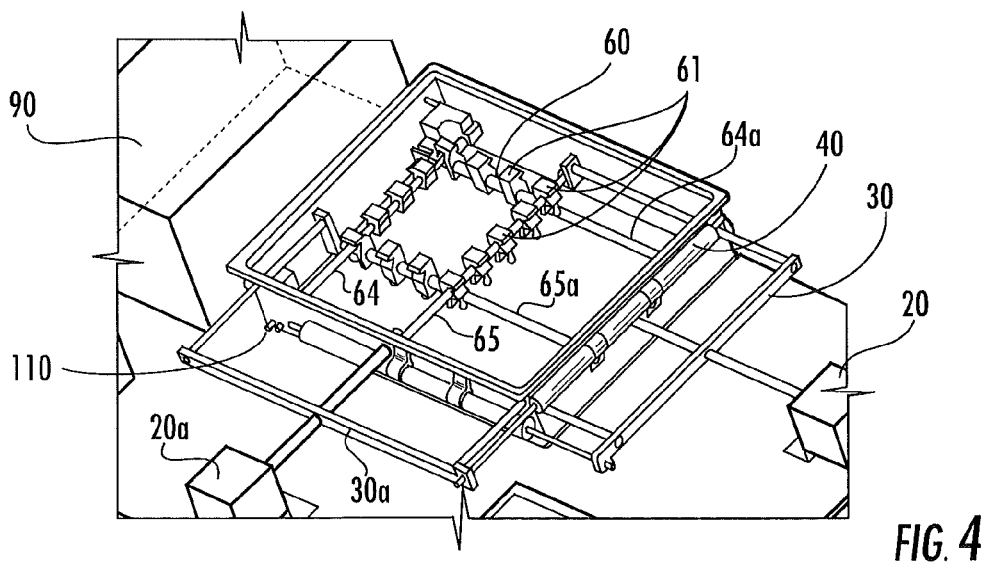
Figure 5:
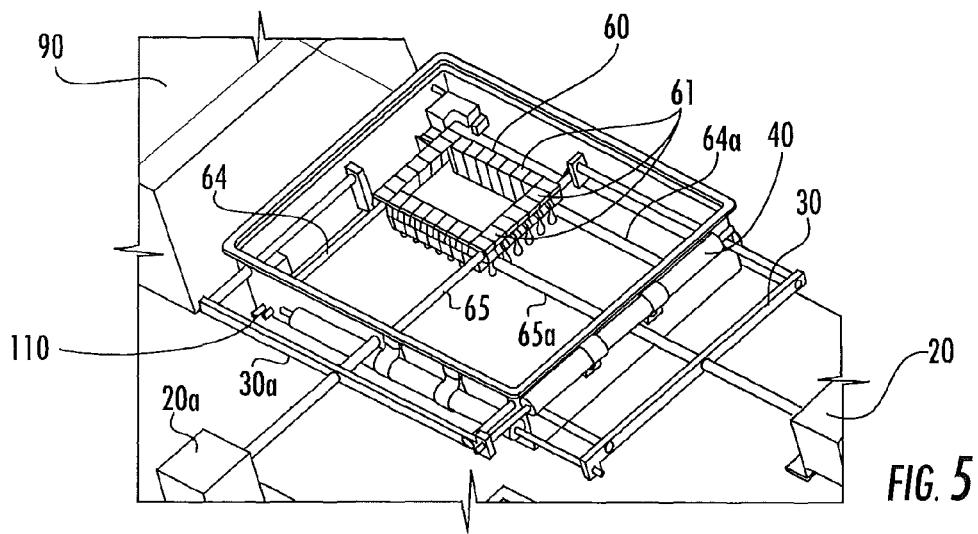
Figure 6:
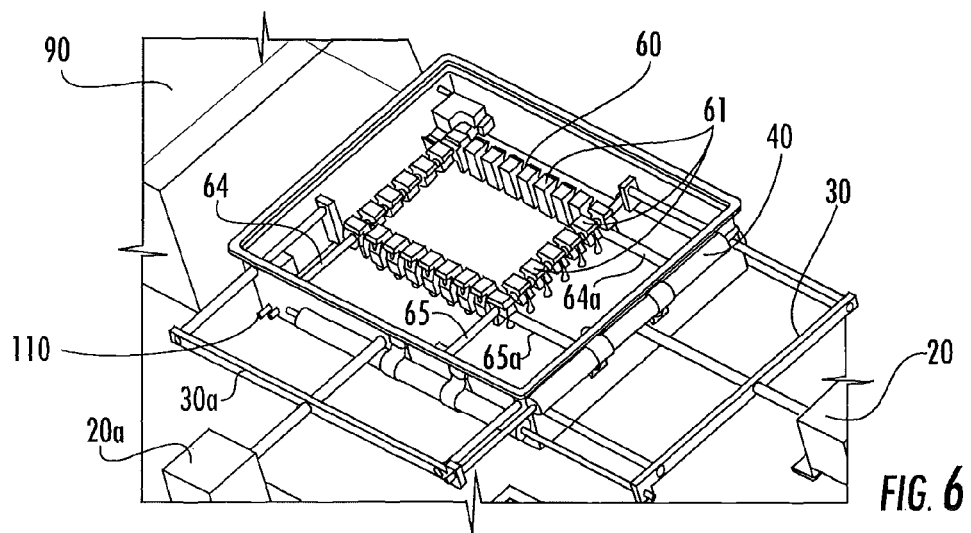
Figure 7:
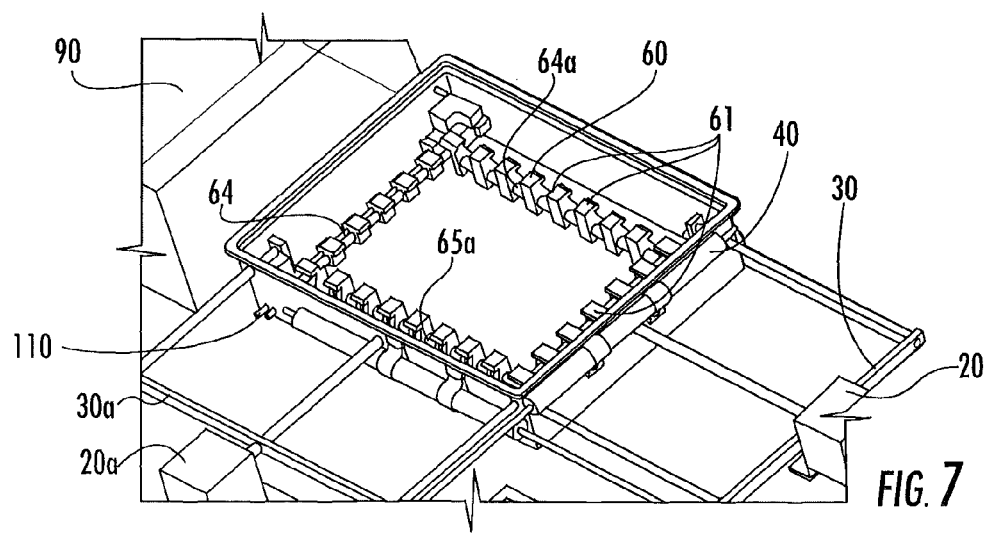
Figure 8:
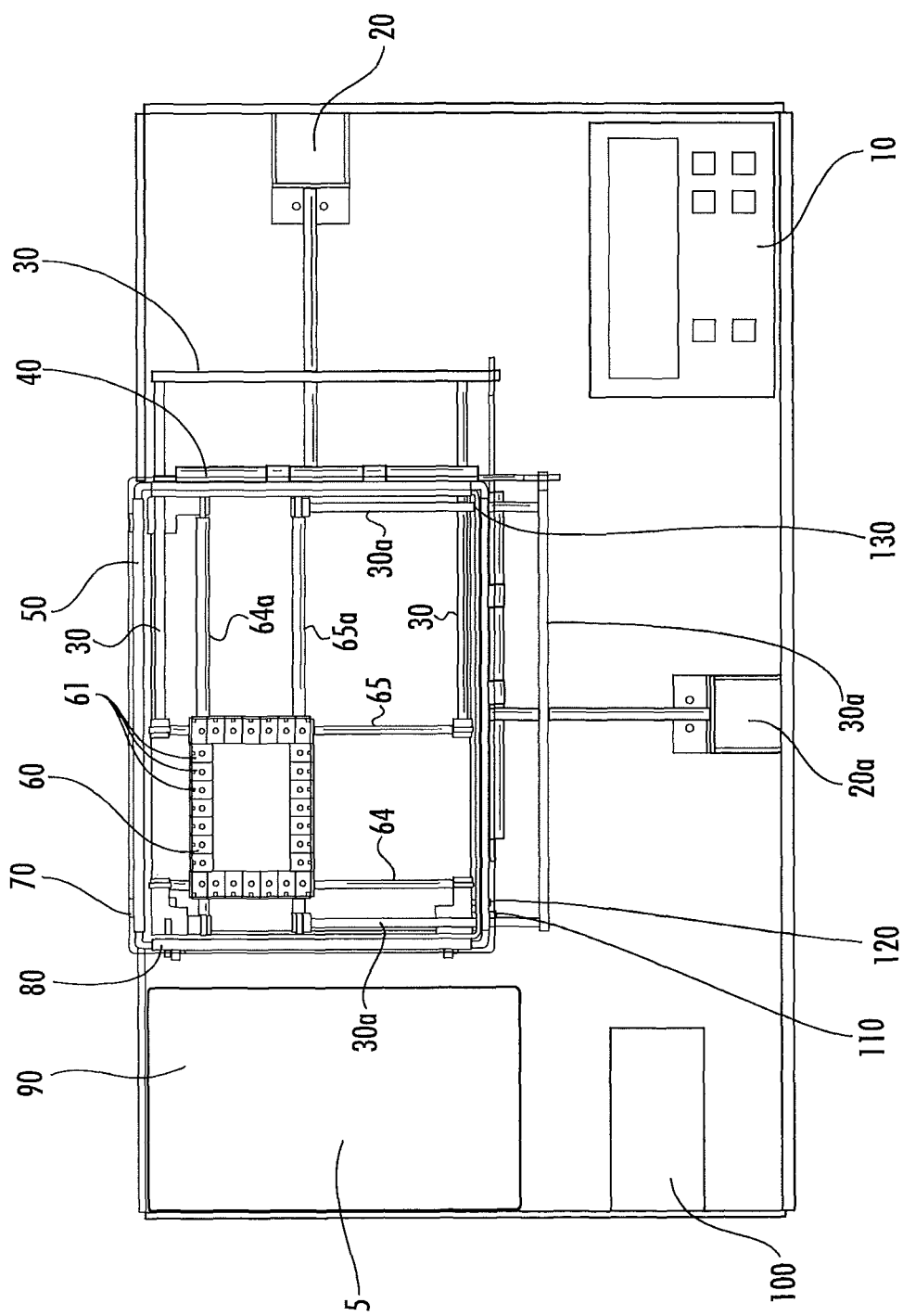
FIG. 8 is a top view of the tissue expander embodiment presented in FIG. 1.

As best seen in FIGS. 2-4 and again FIGS. 5-7 (and in overview in FIG. 8) the clamping member 60 comprises a set of individual clamps 61 (e.g., from 14 to 28 clamps) slidably supported on two pairs of oppositely facing support rods (64, 65, 64a, 65a), with the two pairs of rods positioned in a generally square or rectangular orientation. Support rods 64 and 64a are fixed or "static;" support rods 65 and 65a are travelling or "dynamic" in that they are operatively connected to drive assemblies 30, 30a. Retraction of either drive assembly by its corresponding actuator or motor causes (e.g., when a generally planar tissue is clamped about its periphery by each individual clamp 61) the individual clamps on the generally parallel support rods to become spaced apart: Thus, retraction of drive assembly 30 by actuator 20 causes the clamps 61 slidably mounted on support rods 64, 65 to become spaced apart; retraction of drive assembly 30a by actuator 20a causes the clamps 61 slidably mounted on support rods 64a, 65a to become spaced apart (as shown in FIG. 4 and FIG. 7). Reversing the direction of the actuator or motor 20, 20a causes the corresponding clamps to group closer together, until the individual clamps contact one another (as shown in FIG. 2 and FIG. 5).

The foregoing configuration advantageously stretches tissue in two dimensions. Numerous other configurations can also be used to expand tissue in two dimensions. While pairs of support rods are currently preferred, other embodiments of support pairs can also be used. Flexible rods can be used in place of rigid rods; springs, elastic bands or the like can be used in place of rods. Likewise, while a pair of actuators and a pair of drive assemblies are currently preferred for versatility of control, a single actuator can be employed with a mechanical linkage to both drive assemblies employed. Still further, while two support pairs are illustrated due to the current embodiment of a square or rectangular configuration, other configurations such as triangular, hexagonal, or the like can also be used, with appropriate actuators and drive assemblies. Indeed a spherical configuration can be employed, with individual clamps slidably mounted on a single expandable support structure such as a flexible and/or elastic rod in a round or eliptical orientation, with an actuator operatively associated therewith through a drive assembly for dilating or expanding the diameter of the expandable support.

Figure 9:
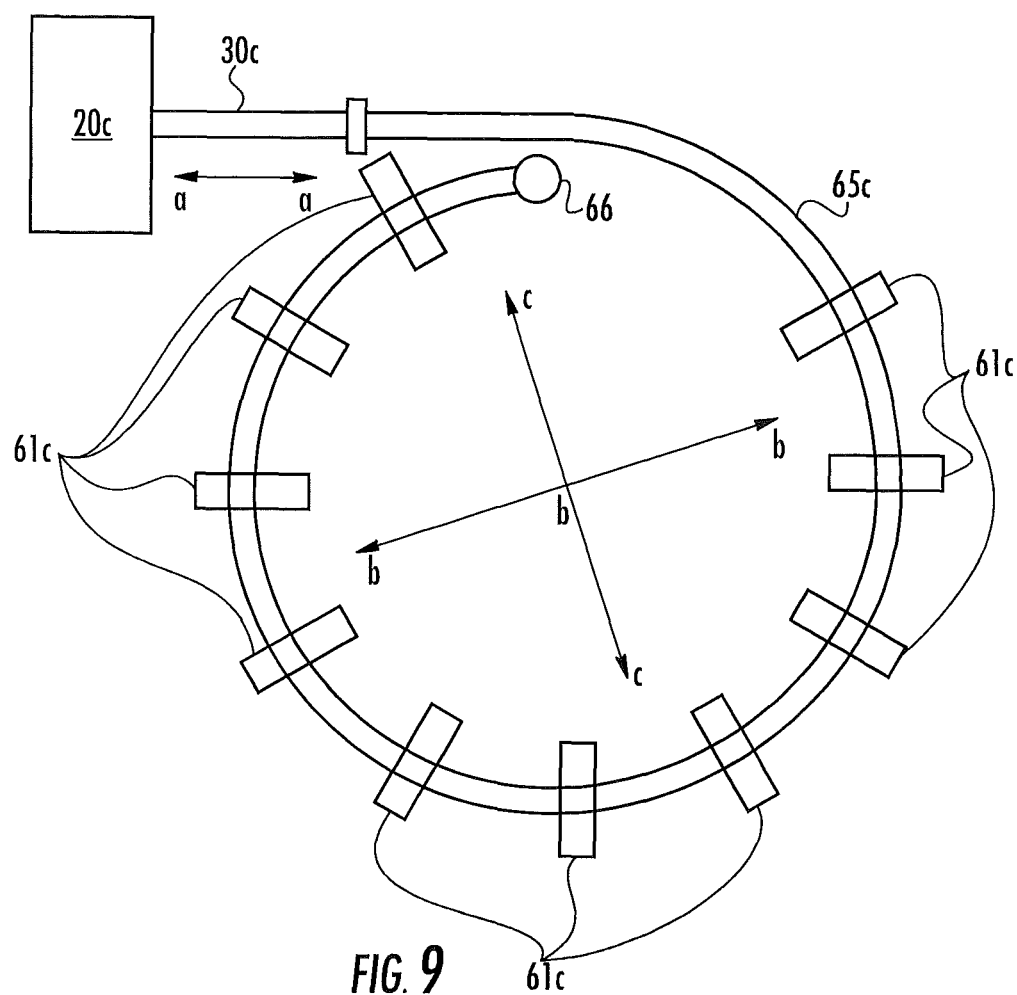
FIG. 9 is a top view of an alternate embodiment of a tissue expander of the present invention.

For example, as shown in FIG. 9, in clamping member 60c the pair of support rods are replaced by a single, flexible, dynamic support rod 65c. Individual clamps 61c are mounted, preferably slidably mounted, on the support rode. One "dynamic" end of support rod 65c is operatively connected to actuator 20c through drive assembly 30c; the other "static" end of the support rod 65c is fixed to anchor member 66. Advancing actuator 30c along dimension a-a causes the area of the clamping member 60 to expand along two axes, along both dimension b-b and dimension c-c; retracting actuator 30c along the same dimension causes the area of the clamping member While the tissue segment is being stretched, the ends of the segment are held in place in the tissue culture by a tissue clamping member (60). In FIGS. 1-8, the tissue clamping member is comprised of a plurality of clamps (61), however, any device that can be used to hold the ends in place can be used. An attachment device is needed for each point to which a force will be applied. Other typical attachment device options include hooks, sutures, and glue. A clamp can be narrow (e.g., less than ¹/₁₀ the length of the edge being held) or broad (up to or greater than the width of the edge, and generally considered broad when greater in width than ½ the width of the edge). If opposed broad clamps are used, stretching between the ends of the clamp will generally be restricted if an orthogonal stretching force is also present on the skin. For maximum stretching efficiency, multiple attachment points capable of moving away from each other during the stretching process are preferred. Multiple clamps (61) attached in a manner that generally forms a rectangular or square tissue clamping member (60) may be used.

The forces, themselves, can be supplied by any means for supplying force, such as a weight, spring, or motor (20). The forces can be either static or dynamic. A static force is one which is applied between two attachment points that do not move further apart from each other as cell growth and division occurs to reduce over time the force between the attachment points. For example, two or more clamps (61) of a tissue clamping member (60) can be attached to opposite ends of a detached skin segment, with the tissue clamping member (60) being operatively connected to an actuator such as a rod assembly (30) such that the distance between the clamps (61) can be varied, which in turn varies the area defined by (inside of) the tissue clamping member (60) along the Z plane of the apparatus (FIG. 1), which is comprised of the Z and X axes. A dynamic force, on the other hand, is one provided between two attachment points that are capable of movement so that a constant force can be maintained. The force on the skin segment is such that an apparatus remains constant as the skin grows and divides. According to some embodiments, the force applied is measured by a force sensor (70) operatively associated with the clamping member (60).

The amount of force applied to the tissue is minimally that required to cause the tissue to stretch. "Stretch" refers to the increase in length and/or area of the tissue along at least one axis, and preferably according to some embodiments along two axes (Z and X in FIG. 1), in response to an applied force. Since the strength of different tissue segments obtained from the same donor vary, the forces are best determined empirically by the amount of tissue stretch that is obtained. A typical stretched skin segment has an area after being subjected to stretching forces (over an appropriate length of time) that is at least twice that of the skin segment prior to being subjected to the stretching forces. For human skin, stretching of at least 2% per day is desired, preferably at least 5%, more preferably at least 10%. Non-human skin can be either tougher or less tough (here "tough" refers to resistance to stretching) than human skin and thus may be stretched correspondingly less or more than these amounts.

In some embodiments, tissue can be stretched until rupture or cell death induced by the tension of stretching, which can readily be followed by histological examination. In some cases it may be desirable to keep stretching under 40 or 50% per day to avoid physical tissue damage such as tearing and/or disruption of tissue matrices. However, some reports state that stretch up to 40% can stimulate skin cells to improve cell survival and matrix secretion.

When tissue is initially placed in the nutrient medium, it should be stretched back to an original in vivo size before actual stretching is measured, since tissue removed from a body generally shrinks to about one-half of its original dimensions. When hair- or fur-bearing skin is being grown, an additional factor to be considered is selecting a stretch rate is the rate of generation of new hair follicles, which will occur along with other cell growth and division in full-thickness skin. The rate of stretching according to some embodiments can be selected in such cases to provide the desired fur (hair) density, rather than simply selecting for the maximum sustainable stretch rate.

Though in some embodiment the device is used to stretch skin, the device is also useful in stretching and/or conditioning and/or culturing other organized tissues, for example, muscle such as skeletal muscle, etc. In addition, the device may be used to condition scaffolds or supports seeded with cells to create a desired tissue.

According to some embodiments, to condition a tissue or support seeded with cells, the method includes: (a) providing tissue or cells on a support (e.g., a collagen support) in a tissue media; then (b) cyclically stretching, and in some embodiments relaxing, the support at least two or three times, up to 5, 10 or 20 times or more, along a first axis and in some embodiment a second axis or direction of travel during a first time period. In some embodiments the first and second axis or direction of travel are substantially perpendicular or orthogonal. Some embodiments also include (c) maintaining the support in a substantially static position during a second time period; and then (d) repeating steps (b) and (c) for a number of times sufficient to produce organized tissue on the solid support from the precursor cells.

"Skin cells" include those cells normally found in skin, and include epidermal cells (e.g., keratinocytes, melanocytes, Merkel cells, Langerhan cells, etc., and any combination thereof) and dermal cells (e.g., fibroblasts, adipocytes, mast cells, macrophages, and any combination thereof). Skin tissue produced by the process of the present invention is useful for grafting onto or implantation into a subject to, for example, treat burns and other wounds such as incisions, lacerations, and crush injuries (e.g., postsurgical wounds, and posttraumatic wounds, venous leg ulcers, diabetic foot ulcers, etc.)

"Muscle cells" include those cells normally found in muscle tissue, including smooth muscle cells, cardiac muscle cells, skeletal muscle cells, and any combination thereof. Muscle cells/tissues produced by the processes described herein are useful for, among other things, implantation into a subject to treat muscle injuries or defects, and/or promote muscle healing.

Precursor or stem cells may also be used to seed supports and appropriately stimulated to differentiate into cells of interest (e.g., skin or muscle cells).

"Supports" on which cells may be seeded and grown to produce cultured tissue of the present invention include any suitable support. See, e.g., U.S. Pat. Nos. 6,998,418; 6,485,723; 6,206,931; 6,051,750; and 5,573,784. Collagen supports or decellularized tissue supports may be used. The length of stretching of the solid support may be to a dimension at least 5% greater in length than the static position, and the relaxing may comprise retracting the support to a dimension not greater in length than the static position. In some embodiments, the "static position" may be intermediate between the stretched and relaxed position, and in such cases the relaxing may comprise retracting the support to a dimension at least 5% lesser in length than the static position.

The first time period, during which the stretching and relaxing occurs, may be of any suitable length, for example from 2 or 3 minutes up to 10, 20 or 30 minutes in duration or more.

The second time period during which the support is maintained in a static position, may be of any suitable duration. In some embodiments the second time period is shorter than the first time period, and may be from 1 or 2 minutes in duration up to 10 or 20 minutes in duration. In other embodiments, the second time period is longer than the first time period, and may be from 10 or 20 minutes in duration up to 40, 60 or 90 minutes in duration, or more. In some embodiments, such as where the first time period contains comparatively long intervals between stretching and relaxing, the need for a second time period may be obviated altogether.

A particular advantage and application of some embodiments of the present invention is its ability to speed, accelerate or enhance the functional maturation or performance of tissues. Thus, in some embodiments the total culturing time of the tissue, such as the repeating of steps (b) and (c) is carried out for a time of up to five days, or a time of up to one, two or three weeks, after which time a contractile response is preferably observed, with shorter culture times being preferred. See also PCT Publication WO 2006/113382.

Tissue (with or without support) produced by the methods of the present invention according to some embodiments is preferably "suturable" in that it has sufficient structural integrity to be surgically sutured or otherwise fastened at either end when grafted or implanted and thereafter develop tension upon contraction.

The foregoing is illustrative of the present invention, and is not to be construed as limiting thereof. The invention is defined by the following claims, with equivalents of the claims to be included therein.

That which is claimed is:
1. A tissue stretching device comprising:
a tissue clamping member comprising from 14 to 28 clamps and defining an area in a Z plane, wherein said tissue clamping member is configured to hold tissue parallel to said Z plane, wherein said tissue clamping member has four sides along the Z plane and is configured to expand in area along the Z plane; wherein said clamps form a rectangular or square tissue clamping member
a displacement sensor operatively associated with said tissue clamping member, said displacement sensor configured to measure a linear displacement along an axis of the Z plane to thereby detect an amount of expansion of the tissue by said tissue clamping member; and
a controller operatively associated with said tissue clamping member, wherein said controller operates an actuator connected to said tissue clamping member to thereby stretch said tissue along the Z plane, wherein said clamps are slidably mounted on two pairs of oppositely facing support rods, wherein one of the pairs of oppositely facing support rods is fixed, and the other of the pairs of oppositely facing support rods is operatively connected to a pair of drive assemblies, wherein said actuator comprises a pair of actuators in which the drive assemblies are operably connected to the pair of actuators.

2. The device of claim 1, wherein said controller is operatively associated with a force sensor, whereby said force sensor senses the force applied to the tissue in said tissue clamping member upon the application of force by said actuator connected thereto.

3. The device of claim 1, wherein said tissue clamping member is enclosed in a chamber configured to hold media, wherein said media is in fluid contact with said tissue clamping member.

4. The device of claim 3 further comprising a media reservoir, and wherein said chamber comprises a media inlet and media outlet, said media inlet being in fluid communication with said media reservoir.

5. The device of claim 3 wherein said chamber further comprises a gas inlet configured to provide a gas to the tissue.

6. The device of claim 1, wherein said tissue clamping member comprises a first set of adjoining sides comprising a first plurality of clamps and a second set of adjoining sides comprising a second plurality of clamps, and wherein the first set of adjoining sides are fixed relative to said chamber, and the second set of adjoining sides are movable along said Z plane.

7. The device of claim 1, wherein the device is configured to stretch skin tissue.

8. The device of claim 1, wherein the device is configured to stretch muscle tissue.

9. A method of stretching a tissue comprising:
clamping the tissue into the device of claim 1; and
stretching the tissue with the device to thereby stretch the tissue.

10. The method of claim 9, wherein the tissue is skin tissue or muscle tissue.

11. A method of treating a skin wound of a subject in need thereof, comprising:
providing a skin tissue;
stretching the skin tissue with the device of claim 1 to form a stretched skin tissue; and then
grafting the stretched skin tissue onto said subject, to thereby treat the skin wound.

12. The method of claim 11, wherein the skin tissue is allogeneic.

13. The method of claim 11, wherein the skin tissue is autologous.

14. A method of culturing organized tissue comprising:
(a) providing cells on a support, wherein said support is clamped into the device of claim 1; then
(b) cyclically stretching and relaxing said support at least twice along a first (X) axis during a first time period;
(c) cyclically stretching and relaxing said support at least twice along a second (Z) axis during said first time period; and then
(d) maintaining said support in a substantially static position during a second time period; and then
(e) repeating steps (b) through (d) for a number of times sufficient to enhance the functionality of the tissue or to produce organized tissue on said solid support from said cells.

15. The method of claim 14, wherein said cyclically stretching and relaxing along said first axis, along said second axis, or along both said first and second axis is carried out at least three times during said first time period.

16. The method of claim 14, wherein said stretching along said first axis, along said second axis, or along both said first and second axis comprises extending said support to a dimension at least 5% greater in length than said static position.

17. The method of claim 14, wherein said relaxing along said first axis, along said second axis, or along both said first and second axis comprises retracting said support to a dimension not greater in length than said static position.

18. The method of claim 14, wherein said relaxing along said first axis, along said second axis, or along both said first and second axis comprises retracting said support to a dimension at least 5% lesser in length than said static position.

19. The method of claim 14, wherein said first time period is from 2 to 30 minutes in duration.

20. The method of claim 14, wherein said second time period is from 10 to 100 minutes in duration.

21. The method of claim 14, wherein said repeating of steps (b) through (d) is carried out for at least one week.

22. The device of claim 1, wherein upon retraction of the pair of drive assemblies by the pair of actuators, the clamps become spaced apart, and upon reversing the direction of the pair of actuators, the clamps group closer together, until individual clamps contact one another.

\* \* \* \* \*